United States Patent
Zabudkin et al.

(10) Patent No.: US 8,802,830 B2
(45) Date of Patent: *Aug. 12, 2014

(54) SYNTHESIS OF EPIRUBICIN FROM 13-DIHYDRODAUNORUBICINE

(75) Inventors: Alexander F. Zabudkin, Donetsk (UA); Victor Matvienko, Donetsk (UA); Aleksandr M. Itkin, San Diego, CA (US); Alexey Matveev, Donetsk (UA)

(73) Assignee: Solux Corporation, San Diego, CA (US)

( * ) Notice: Subject to any disclaimer, the term of this patent is extended or adjusted under 35 U.S.C. 154(b) by 1387 days.

This patent is subject to a terminal disclaimer.

(21) Appl. No.: 11/612,322

(22) Filed: Dec. 18, 2006

(65) Prior Publication Data

US 2007/0142309 A1 Jun. 21, 2007

Related U.S. Application Data

(60) Provisional application No. 60/751,765, filed on Dec. 20, 2005.

(51) Int. Cl.
*C07H 15/24* (2006.01)
*A61K 31/704* (2006.01)

(52) U.S. Cl.
USPC ............................................. 536/6.4; 514/34

(58) Field of Classification Search
USPC ............................................. 536/6.4; 514/34
See application file for complete search history.

(56) References Cited

U.S. PATENT DOCUMENTS

| | | | |
|---|---|---|---|
| 3,803,124 A | 4/1974 | Arcamone | |
| 4,112,076 A | 9/1978 | Arcamone | |
| 4,188,377 A | 2/1980 | Suarato et al. | |
| 4,211,864 A | 7/1980 | Vicario et al. | |
| 4,225,589 A | 9/1980 | Ducep et al. | |
| 4,345,068 A | 8/1982 | Suarato | |
| 4,861,870 A | 8/1989 | Oppico | |
| 5,091,373 A | 2/1992 | Gatti et al. | |
| 5,103,029 A | 4/1992 | Cabri et al. | |
| 5,587,495 A | 12/1996 | Cabri et al. | |
| 5,731,313 A | 3/1998 | Suarato et al. | |
| 5,814,608 A | 9/1998 | Animati et al. | |
| 5,874,550 A | 2/1999 | van der Rijst et al. | |
| 5,945,518 A | 8/1999 | Bigatti | |
| 5,998,615 A | 12/1999 | Suarato et al. | |
| 6,087,340 A | 7/2000 | Gatti | |
| 6,096,888 A | 8/2000 | Suarato et al. | |
| 6,376,469 B1* | 4/2002 | Shimago et al. | 514/34 |
| 6,653,455 B1 | 11/2003 | Johdo et al. | |
| 6,673,907 B2* | 1/2004 | Priebe et al. | 536/6.4 |
| 7,053,191 B2 | 5/2006 | Zabudkin et al. | |
| 7,109,177 B2* | 9/2006 | Priebe et al. | 514/34 |
| 7,388,083 B2 | 6/2008 | Matvienko et al. | |
| 7,485,707 B2 | 2/2009 | Matvienko et al. | |
| 7,557,090 B2* | 7/2009 | Priebe et al. | 514/34 |
| 2006/0063726 A1 | 3/2006 | Matvienko et al. | |
| 2006/0223766 A1 | 10/2006 | Matvienko et al. | |
| 2007/0037758 A1 | 2/2007 | Priebe et al. | |
| 2007/0135624 A1* | 6/2007 | Zabudkin et al. | 536/6.4 |

FOREIGN PATENT DOCUMENTS

| | | |
|---|---|---|
| EP | 0 014 425 A1 | 8/1980 |
| EP | 0 253 654 A2 | 1/1988 |
| EP | 0328399 | 8/1989 |
| IT | 1196154 | 11/1988 |
| JP | 2002-255888 A | 11/2002 |
| UA | 50928 A | 11/2002 |
| WO | WO86/00073 A1 | 1/1986 |
| WO | WO96/29335 A1 | 9/1996 |

OTHER PUBLICATIONS

Dorwald, F. A., Side Reactions in Organic Synthesis, 2005, Wiley: VCH, Weinheim p. IX of Preface.*
A. Bisai et al. /Tetrahedron Letters 43 (2002) 8355-8357.*
PCT International Search Report for PCT/US2004/20679, Applicant: Solux Corporation, Form PCT/ISA/220, dated May 4, 2006 (5 pages).
PCT Written Opinion for PCT/US2004/20679, Applicant: Solux Corporation, Form PCT/ISA/237, dated May 4, 2006 (4 pages).
Y. Kimura, et al., Tirmethylsilyl Trifluoromethanesulfonate as an Excellent Gludosidation Reagent for Antracycline Synthesis. Simple and Efficient Synthesis of Optically Pure 4-Demetrhoxydaunorubicin, Terashima. Chem. Letters, 1984, pp. 501-504.
PCT International Search Report for PCT/US2006/07987, Applicant: Solux Corporation, Form PCT/ISA/220, dated Jul. 28, 2006 (4 pages).
PCT International Search Report for PCT/US2006/61978, Applicant: Solux Corporation, Form PCT/ISA/210 and 220, dated Jan. 10, 2008 (4 pages).
PCT Written Opinion for PCT/US2006/61978, Applicant: Solux Corporation, Form PCT/ISA/237, dated Jan. 10, 2008 (4 pages).
PCT Written Opinion for PCT/US2006/07987, Applicant: Solux Corporation, Form PCT/ISA/237, dated Jul. 28, 2006 (4 pages).
Office Action dated Jun. 13, 2006 for related U.S. Appl. No. 10/877,221, filed Jun. 25, 2004, Inventor: Victor Matvienko (7 pages).
Amendment dated Sep. 13, 2006 for related U.S. Appl. No. 10/877,221, filed Jun. 25, 2004, Inventor: Victor Matvienko (9 pages).

(Continued)

*Primary Examiner* — Sabiha Qazi
(74) *Attorney, Agent, or Firm* — Vista IP Law Group LLP

(57) ABSTRACT

A method of preparing an anthracyclin such as epirubicin from a starting material comprising 13-dihydrodaunorubicine (13-daunorubicinol). The method comprises producing N-Trifluoroacetyl-13-daunorubicinol from 13-daunorubicinol by acylation. The N-Trifluoroacetyl-13-daunorubicinol is reacted with an aprotic solvent and an acylating agent to produce an intermediate sulfoxy salt which is treated with a strong base to produce 4'-keto-N-Trifluoroacetyldaunorubicin. The 4'-keto-N-Trifluoroacetyldaunorubicin is reacted with a reducing agent, such as borohydride of an alkaline metal, to produce N-Trifluoroacetyl-4'-epi-daunorubicin. The N-Trifluoroacetyl-4'-epi-daunorubicin is hydrolyzed in a basic solution to produce an intermediate compound. The intermediate compound is reacted with a halogenizing agent to produce a 14-Hal-derivative. The 14-Hal derivative is hydrolized in the presence of a formate of an alkaline metal to produce the desired final compound.

32 Claims, No Drawings

(56) References Cited

OTHER PUBLICATIONS

Office Action dated Oct. 24, 2006 for related U.S. Appl. No. 10/877,221, filed Jun. 25, 2004, Inventor: Victor Matvienko (7 pages).
Amendment dated Jan. 23, 2007 for related U.S. Appl. No. 10/877,221, filed Jun. 25, 2004, Inventor: Victor Matvienko (9 pages).
Office Action dated Mar. 16, 2007 for related U.S. Appl. No. 10/877,221, filed Jun. 25, 2004, Inventor: Victor Matvienko (6 pages).
Amendment dated Sep. 17, 2007 for related U.S. Appl. No. 10/877,221, filed Jun. 25, 2004, Inventor: Victor Matvienko (11 pages).
Declaration of Philipp Alexander Titulsi under 37 C.F.R. 1.132 dated Sep. 13, 2007, for related U.S. Appl. No. 10/877,221, filed Jun. 25, 2004, Inventor: Victor Matvienko (3 pages).
Declaration of Anil Dhedia under 37 C.F.R. 1.132 dated Sep. 13, 2007, for related U.S. Appl. No. 10/877,221, filed Jun. 25, 2004, Inventor: Victor Matvienko (2 pages).
Declaration of Dr. Waldemar Priebe under 37 C.F.R. 1.132 dated Sep. 15, 2007, for related U.S. Appl. No. 10/877,221, filed Jun. 25, 2004, Inventor: Victor Matvienko (38 pages).
Office Action dated Nov. 6, 2007 for related U.S. Appl. No. 10/877,221, filed Jun. 25, 2004, Inventor: Victor Matvienko (6 pages).
Office Action dated Dec. 11, 2007 for related U.S. Appl. No. 10/877,221, filed Jun. 25, 2004, Inventor: Victor Matvienko (4 pages).
Office Action dated Jun. 1, 2007 for related U.S. Appl. No. 11/367,742, filed Mar. 4, 2006, Inventor: Victor Matvienko (8 pages).
Amendment dated Dec. 3, 2007 for related U.S. Appl. No. 11/367,742, filed Mar. 4, 2006, Inventor: Victor Matvienko (10 pages).
Notice of Allowance dated Feb. 8, 2008 for related U.S. Appl. No. 11/367,742, filed Mar. 4, 2006, Inventor: Victor Matvienko (8 pages).
PCT International Search Report for PCT/US2006/62286, Applicant: Solux Corporation et al., Forms PCT/ISA/220 and 210, dated Sep. 24, 2007 (3 pages).
PCT Written Opinion for PCT/US2006/62286, Applicant: Solux Corporation et al., Forms PCT/ISA/237, dated Sep. 24, 2007 (5 pages).
PCT International Preliminary Report on Patentability for PCT/US2006/62286, Applicant: Solux Corporation et al., Forms PCT/IB/326, 373 and PCT/ISA/237, dated Jul. 3, 2008 (7 pages).
PCT International Preliminary Report on Patentability for PCT/US2006/061978, Applicant: Solux Corporation et al., Forms PCT/IB/326, 373 and PCT/ISA/237, dated Jun. 26, 2008 (5 pages).
Amendment and Response dated Feb. 21, 2008 for U.S. Appl. No. 10/877,221, filed Jun. 25, 2004, inventor: Victor Matvienko (10 pages).
Office Action dated Jun. 9, 2008 for U.S. Appl. No. 10/877,221, filed Jun. 25, 2004, inventor: Victor Matvienko (5 pages).
Amendment After Final dated Aug. 1, 2008 for U.S. Appl. No. 10/877,221, filed Jun. 25, 2004, inventor: Victor Matvienko (7 pages).
Notice of Allowance dated Aug. 20, 2008 and Supplemental Notice of Allowability dated Oct. 31, 2008 for U.S. Appl. No. 10/877,221, filed Jun. 25, 2004, inventor: Victor Matvienko (10 pages).
PCT International Search Report for PCT/US08/86088, Applicant: Solux Corporation, Form PCT/ISA/210 and 220, dated Jan. 26, 2009 (4 pages).
PCT Written Opinion of the International Search Authority for PCT/US08/86088, Applicant: Solux Corporation, Form PCT/ISA/237, dated Jan. 26, 2009 (3 pages).
Chinese Office Action dated May 18, 2011 for CN Application No. 200680047939.7, filed Dec. 19, 2006, Applicant: Solux Corporation (9 pages).
Chinese Office Action dated Aug. 20, 2010 for CN Application No. 200680047939.7, filed Dec. 19, 2006, Applicant: Solux Corporation (10 pages).
International Report on Patentability dated Jul. 22, 2010 for PCT/US20081086088, filed Dec. 9, 2008, Applicant: Solux Corporation (6 pages).
Chinese Office Action dated Nov. 15, 2010 for 200680046948.4, filed Dec. 13, 2006, Applicant: Solux Corporation (7 pages).
Russian Office Action dated Jul. 20, 2010 for PCT/US2006/062286, filed Dec. 19, 2006, Applicant: Solux Corporation (3 pages).
Notice of Allowance dated Oct. 31, 2008 for U.S. Appl. No. 10/877,221, filed Jun. 25, 2004, Inventor: Victor Matvienko, (6 pages).
International Preliminary Report on Patentability dated Jun. 15, 2006 for PCT/US2004/020679, filed Jun. 25, 2004, Applicant: Solux Corporation (5 pages).
Chinese Office Action dated Apr. 27, 2007 for CN Application No. 200480013747.5, filed May 20, 2004, Applicant: Solux Corporation (6 pages).
Chinese Office Action dated Feb. 21, 2008 for CN Application No. 200480019127.2, filed Jun. 25, 2004, Applicant: Solux Corporation (6 pages).
Chinese Office Action dated Sep. 7, 2007 for CN Application No. 200480019127.2, filed Jun. 25, 2004, Applicant: Solux Corporation (9 pages).
Russian Office Action dated Dec. 23, 2007 for RU Application No. 2006101764, filed Jan. 24, 2006, Applicant: Solux Corporation (5 pages).
Russian Office Action dated Jun. 4, 2007 for RU Application No. 2006101764, filed Jan. 24, 2006, Applicant: Solux Corporation (3 pages).
Russian Office Action dated Nov. 13, 2007 for RU Application No. 2006101764, filed Jan. 24, 2006, Applicant: Solux Corporation (6 pages).
The Structure of Carminomycin I, Journal of the Americal Chemical Society, 97:25, Dec. 10, 1975.
Chrisman, W. et al., The Effect of Different Amine Bases in the Swern Oxidation of B-Amino Alcohol+, Tetrahedron Letters, vol. 38, No. 12, pp. 2053-2056, 1997.
Complaint for Declaration Judgment filed in the United States District Court Southern District of California on Dec. 28, 2011, Plaintiff, *Synbias Pharma* vs. Defendant, *Solux Corporation* (19pages).
PCT International Preliminary Report on Patentability (Chapter I of the Patent Cooperation Treaty) for PCT/US2006/007987, Applicant: Solux Corporation et al., Form PCT/IB/326 and 373, dated Sep. 20, 2007 (6pages).
Extended European Search Report dated Jul. 14, 2010 in European Patent Application No. 06748302.4-2123/2187891, Applicant: Solux Corporation (5pages).
Rodygin, M. Yu, et al., Selective Monobromination of Ketones by Bis(Dimethylacetamide)Hydrogen Tribromide, 6064 Russian Journal of Organic Chemistry 30 (Jun. 1994), No. 6, Part 1, New York, US; L.M. Litvinenko Institute of Physical Organic Chemistry and Coal Chemistry, National Academy of Sciences of Ukraine, Donetsk. Translated from Zhurnal Organicheskoi Khimii, vol. 30, No. 6, pp. 827-832, Jun. 1994. Original article submitted Apr. 27, 1994.
Observations by Third Parties Pursuant to Article 115 EPC in European Application No. EP 06 748 302.4, Publication No. EP 2 187 891 A1, Applicant: Solux Corporation (4pages).
Declaration Patent for an Invention in UA 50928A, Applicant: Scientific Production Company "Synbias Pharma" (1page) including issued patent UA 50928A (10pages).
Office Communication dated May 25, 2011 in European Patent Application No. 06 748 302.4-2123, Applicant: Solux Corporation (6pages).
Response to Office Communication dated Oct. 4, 2011 in European Patent Application No. 06 748 302.4-2123, Applicant: Solux Corporation (9pages).

* cited by examiner

SYNTHESIS OF EPIRUBICIN FROM 13-DIHYDRODAUNORUBICINE

RELATED APPLICATIONS

This Application claims the benefit of U.S. provisional Application No. 60/751,765, filed on Dec. 20, 2005, in accordance with 35 U.S.C. Section 119(e), and any other applicable laws. U.S. provisional Application No. 60/751,765 is hereby incorporated by reference in its entirety as if set forth fully herein.

FIELD OF THE INVENTION

The field of the invention generally relates to chemical methods used to produce anthracyclines, a compound which is useful as an anticancer chemotherapeutic drug. More specifically, the field of the invention relates to methods of producing anthracyclines in the form of Formula (1) (wherein $An^-$ is an anion of any strong acid; for example, in one non-limiting case of 4'-epirubicin, $An^-$ comprises $Cl^-$).

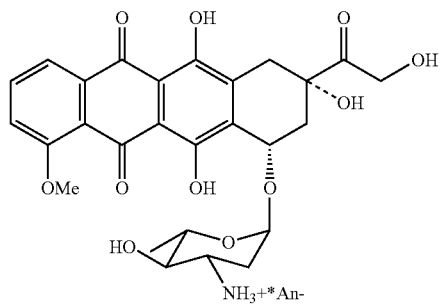

Formula 1

BACKGROUND OF THE INVENTION

Anthracyclines form one of the largest families of naturally occurring bioactive compounds. Several members of this family have shown to be clinically effective anti-neoplastic agents. These include, for example, daunorubicin, doxorubicin, idarubicin, epirubicin, pirarubicin, zorubicin, aclarubicin, and carminomycin. For instance, these compounds have shown to be useful in treatment of breast carcinoma, acute lymphocytic and non-lymphocytic leukemia, chronic lymphocytic leukemia, non-Hodgkin's lymphoma, and other solid cancerous tumors.

Anthracyclin antibiotics possess very high antineoplastic activity allowing for their effective application in the treatment of a wide spectrum of tumors. The starting material for the synthesis of the majority of anthracyclin antibiotics is Daunorubicin having the form shown in Formula (2). Epirubicin of Formula (1) differs from Daunorubicin which is produced by fermentation, by having a 14-oxymethyl group and equatorial orientation of the HO-4'-C.

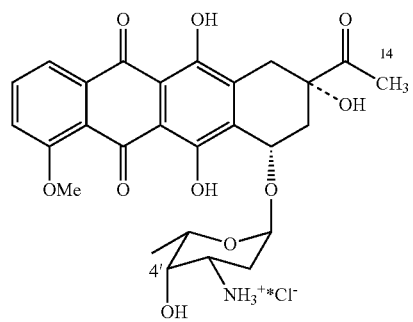

Formula 2

Conversion of Daunorubicin to Epirubicin is achieved by the oxidation of 4'-hydroxyl fragment to ketone, accompanied by a loss of the optical center, with additional stereospecific reduction (in a needed conformation) and further transformation of the epi-daunorubicin to epirubicin via bromination of the 14-$CH_3$—(CO)-fragment and hydrolysis of the resulting 14-$CH_2Br$-fragment to-(CO)—$CH_2OH$ radical. This process is shown diagrammatically in Diagram 1, below.

Diagram 1.

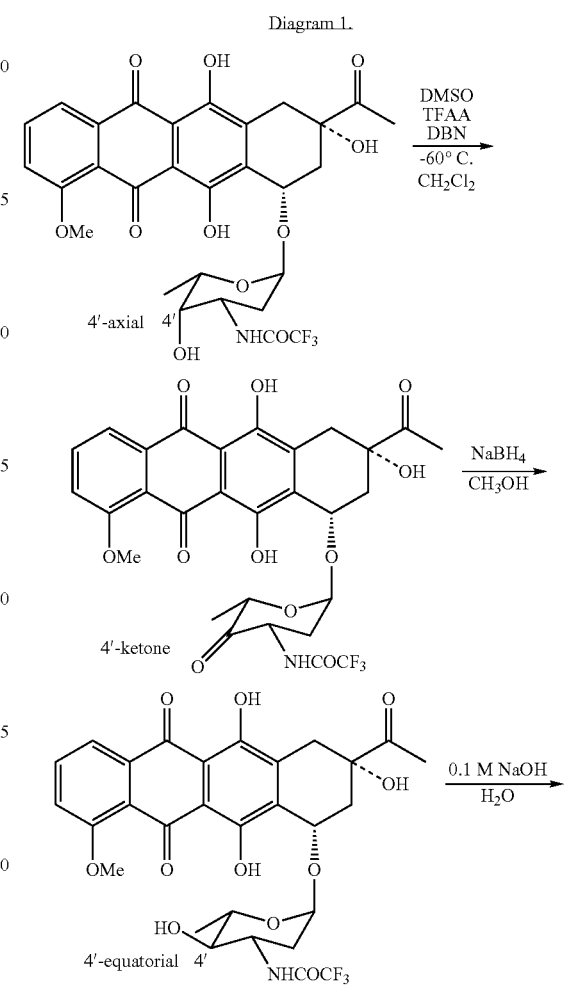

-continued

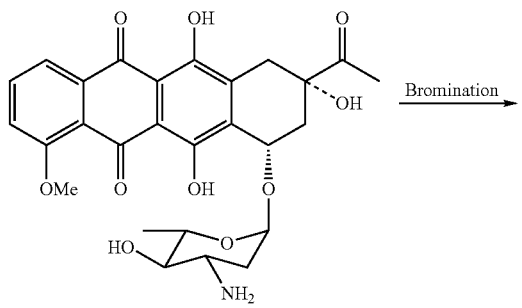

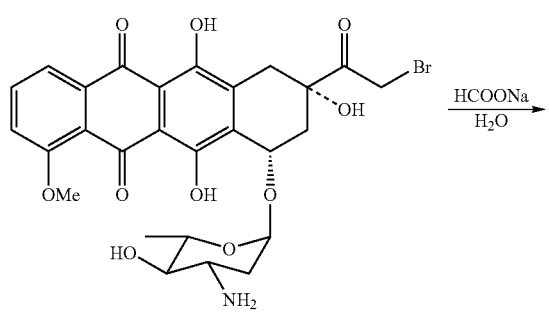

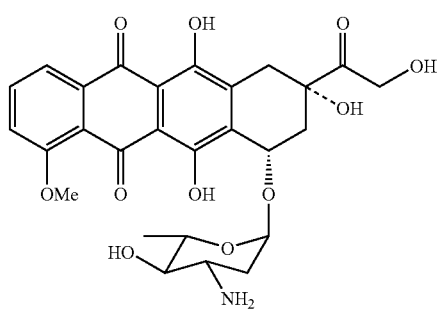 [SMILES: COc1cccc2c1C(=O)c1c(O)c3c(c(O)c1C2=O)C[C@@](O)(C(=O)CO)C[C@@H]3OC1CC(N)C(O)C(C)O1]

This synthetic pathway was developed by Farmitalia as described in U.S. Pat. No. 4,345,068 to Suarato et al. Other methods of epi-daunorubicin synthesis have been previously described, for example, in U.S. Pat. No. 5,945,518 to Bigatti et al. and U.S. Pat. No. 5,874,550 to van der Rijst et al. However, all existing methods of synthesizing epi-daunorubicin utilize the same starting material, namely Daunorubicin of Formula (2).

SUMMARY OF THE INVENTION

The present invention is directed to an innovative method for producing an epirubicin compound using a new starting material for its synthesis. Specifically, the new starting material is 13-daunorubicinol (13-dihydrodaunorubicin as shown in Formula (3)). The key difference between daunorubicinol and daunorubicin is the presence of a hydroxyl group in position 13 of the anthracyclin nucleus as opposed to a 13-keto group.

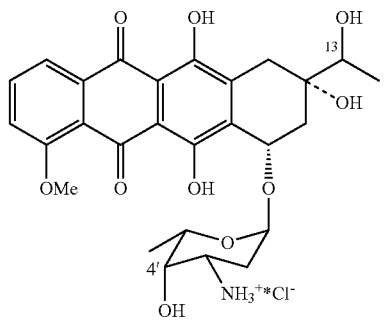

Formula 3

The steps involved in the novel process of the present invention are as follows:

(1) the first stage of the new process is the selective placement of the protective group on the amino-group of the antibiotic's glycoside part, as shown in Formula (4); the 13-OH and 4'-OH groups preferably remain unmodified.

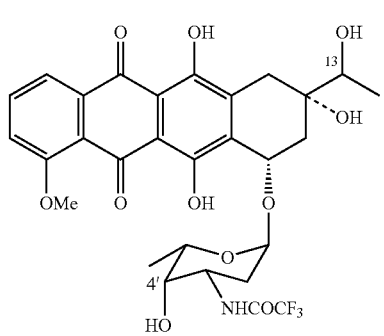

Formula 4

(2) the second stage of the process involves oxidation of the 13-OH and 4'-OH groups to the corresponding ketones by treating the N-Trifluoroacetyl-13-daunorubicinol of Formula (4), with dimethylsulfoxide activated by different acylating agents (AcX), to produce the compound as shown in Formula (5):

AcX=PySO$_3$, SOCl$_2$, PHal$_3$, POHal$_3$; Hal=Cl, Br;

Ac=AlkCO; OC—(CH$_2$)$_n$—CO, n=0-4; AlkSO$_2$; ArCO; ArSO$_2$,

Alk=alkyl of halogenalkyl radical

Ar=phenyl or substituted phenyl radical

X=Cl, Br, I, OAc.

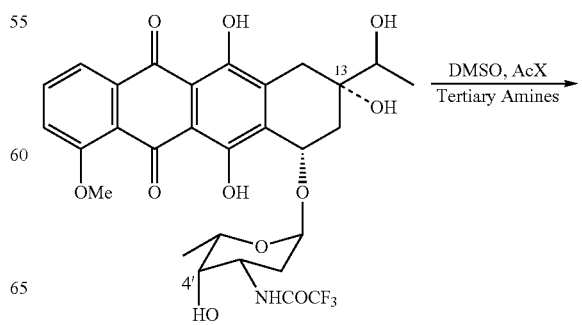

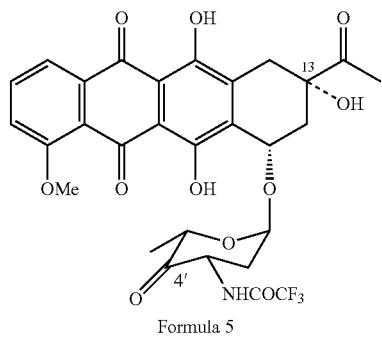

Formula 5

(3) during the third stage, the 4'-keto group of the 4'-keto-N-Trifluoroacetyl-daunorubicin of Formula (5), is reduced to the equatorial 4'-OH group, without modification of the 13-keto group. This is accomplished by reacting the 4'-keto-N-Trifluoroacetyl-daunorubicin with a reducing agent, such as a derivative of a borohydride of an alkaline metal $MHBL_3$, where M=Li, Na, K; L=AlkO, AlkCOO, ArCOO (Alk=Me, Et, n-Pr, All, $-(CH_2)_n$, n=0-4; Ar=Ph or subst. Ph=Ph-Alk, resulting in the N-Trifluoroacetyl-4'-epi-daunorubicin as shown in Formula (6).

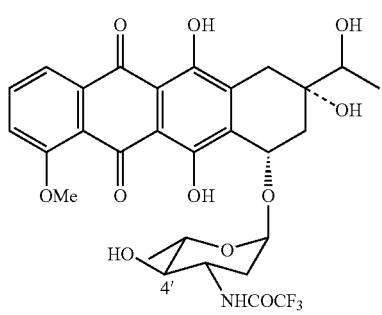

Formula 6

(4) hydrolyzing N-Trifluoroacetyl-4'-epi-daunorubicin in a basic solution to produce a derivative as shown in Formula (7).

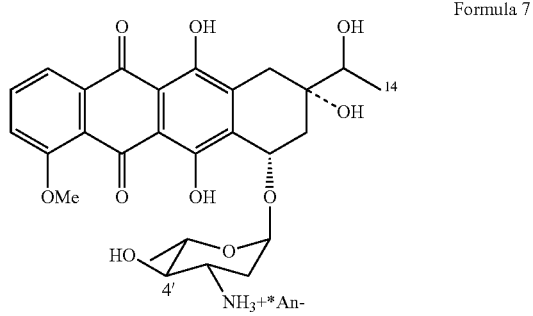

Formula 7

(5) halogenization of the 4'-epi-daunorubicin of Formula (7) at the C14 position is accomplished by reaction with the complex halogenides described by Formula (8):

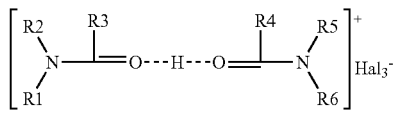

Formula 8 where $R_1$ through $R_6$ are defined as H or a hydrocarbon radical of 1 to 4 carbon chains ($C_1$-$C_4$); Hal is Cl, Br, I.

(6) the attained 14-Hal-derivative, as shown in Formula (9) (where Hal is Cl, Br, or I; and An⁻ is an anion of a strong acid), is hydrolyzed by well-known methods in the presence of a formate of an alkaline metal with a final result of a product of Formula (1).

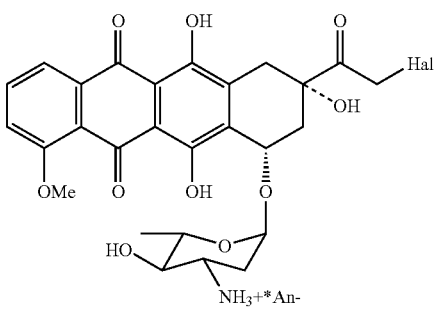

Formula 9

DETAILED DESCRIPTION OF THE INVENTION the method of preparing an epirubicin compound using daunorubicinol as the starting material according to the present invention comprises the following steps.

I. Synthesis of N-trifluoroacetyl-13-daunorubicinol

N-TFA-13-daunorubicinol is produced from 13-daunorubicinol by acylation of the latter by trifluoroacetic anhydride in dry, aprotonic, immiscible-with-water solvents, preferably in dichloromethane, with further soft hydrolysis of the resulting amidoester in a two-phase system of aqueous base—organic solution of the amidoester to N-TFA-Daunorubicinol (this is shown in Diagram 2, below).

Diagram 2

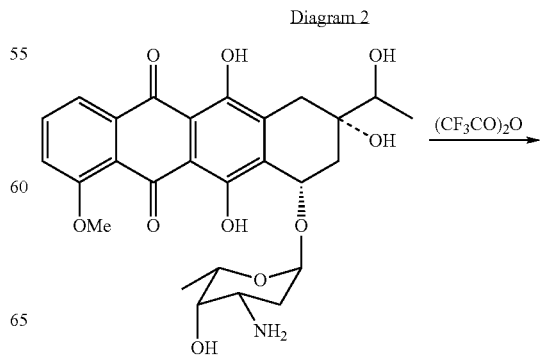

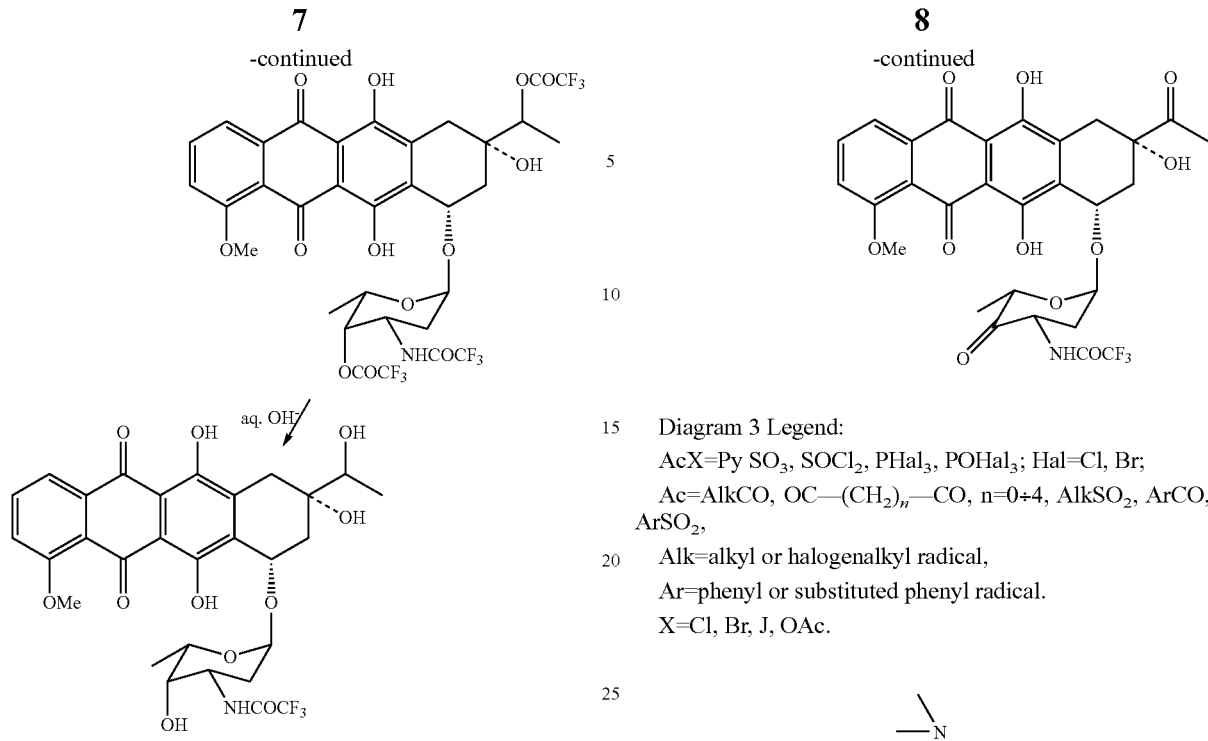

Diagram 3 Legend:
AcX=Py SO$_3$, SOCl$_2$, PHal$_3$, POHal$_3$; Hal=Cl, Br;
Ac=AlkCO, OC—(CH$_2$)$_n$—CO, n=0÷4, AlkSO$_2$, ArCO, ArSO$_2$,
Alk=alkyl or halogenalkyl radical,
Ar=phenyl or substituted phenyl radical.
X=Cl, Br, J, OAc.

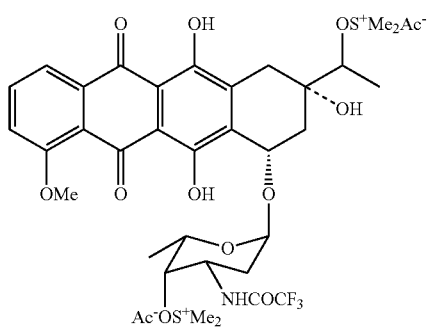

R$_7$, R$_8$, R$_9$=alkyl or cycloalkyl;
R$_8$, R$_9$=—(CH$_2$)$_n$— where n=3 to 6. cyclic of polycyclic highly basic amine, for example DBU, quinuclidine.

Aprotic solvent=non-aqueous, aprotic solvent, for example DMSO, DMAA, HMPA, DCM, and other halogenalkanes, aromatic hydrocarbons, and mixtures thereof.

Reaction is conducted at temperatures from −80° C. to 0° C.; more optimally at −70±5° C. Increasing the reaction temperature significantly increases the amount of side products and impurities.

III. Synthesis of 4'-epi-N-trifluoroacetyldaunorubicin

4'-epi-N-trifluoroacetyldaunorubicin is synthesized by way of stereospecific reduction of the 4'-keto-N-TFA-daunorubicin in equatorial conformation with sodium borohydride (L=H).

This reaction (see Diagram 4) increases yield of the desired epimer to more than 90%. However, utilization of this reducing agent also leads to a reduction of the 13-keto-group in the aglycon fragment of the molecule with formation of N-TFA-daunorubicinol.

II. Synthesis of 4'-keto-N-trifluoroacetyldaunorubicin

4'-keto-N-TNF-daunorubicin is derived by interacting N-TFA-13-daunorubicinol with dimethylsulfoxide, activated by various acetylating agents (AcX). N-TFA-13-daunorubicinol is converted to its sulfoxy salt (4), which further splits to 4'-keto-N-TFA-daunorubicin (as shown in Formula (10), among other products.

Formula 10

In certain conditions, the yield of the target ketone may exceed 85% (see Diagram 3).

Diagram 3

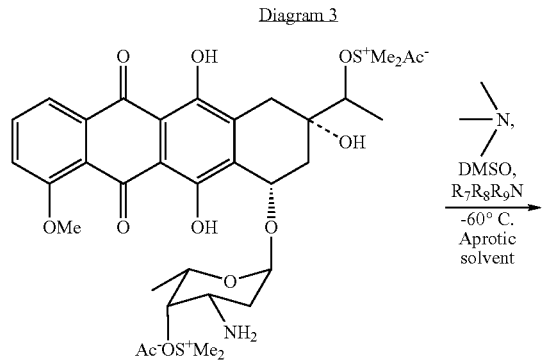

Diagram 4

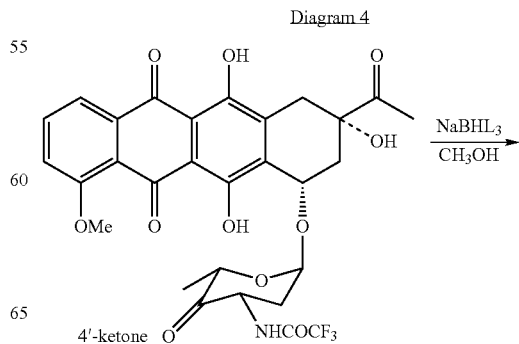

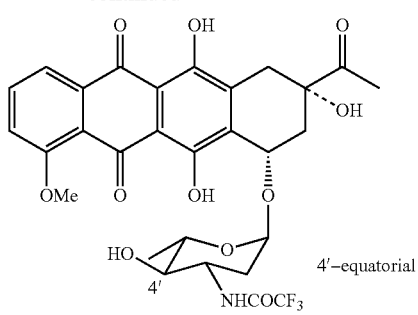

4'-equatorial

Alternatively, the reducing agent may be sodium borohydride with L≠H; in particular, L=AlkO (Alk=Me, Et, n-Pr, All); AcO (Ac=CR₃CO, R═H, Hal). Utilization of this borohydride decreases its reducing power, thus improving both regio-and stereoselectivity of the reaction.

The reaction is conducted in non-reducible solvents, such as alcohols, ethers, hydrocarbons and halogenated hydrocarbons and mixtures thereof, preferably in methanol. The reaction is conducted at temperatures from −35° C. to 10° C., and more preferably at −20±5° C.

The transformation of 4'-epi-N-TFA-daunorubicin to 4'-epi-daunorubicin by removal of the trifluoroacetyl protection group from 4'-epi-N-TFA derivatives of anthracyclins is attained by treatment with an aqueous base having a pH=10-13, at a temperature from 0° C. to 40° C., preferably 20±5° C.

IV. Modification of 14-CH3 radical to 14-CH2OH in an aglycone fragment of 4'-epi-daunorubicin Halogenization of the 4'-epi-daunorubicin product (Formula (6)) shown in Diagram (4) is accomplished by utilization of complex halogenides as halogenizing agents. This approach decreases the number of synthesizing stages, and increases the yield and purity of the final product.

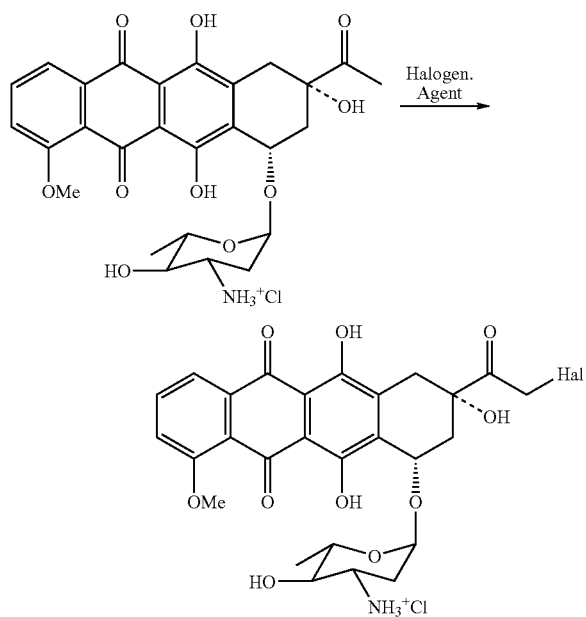

Diagram 5

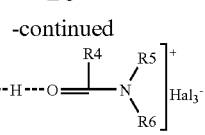

Solvents utilized in this reaction are amides, simple ethers and mixtures thereof; preferably dimethylformamide and tetrahydrofuran.

This reaction is conducted at a temperature of 20-60° C. for 2-20 hours; preferably at 50° C. for 3 hours. The attained 14-halogen derivative (Formula (9) is hydrolyzed in an aqueous acetone solution in the presence of salts of carboxylic acids, preferably sodium formate, pH=2.5-5.5. This results in the final product of Formula (1).

EXAMPLE 1

(a) 5 grams of 13-dihydrodaunorubicine of Formula (3) is suspended in 200 ml of dichloromethane (DCM) and chilled to 0° C. While intensely stirring the suspension, drops of trifluoroacetic anhydride in DCM (8 ml:15 ml) are slowly added over a period of 1 hour.

(b) The resulting mixture is kept at 0° C. for another 0.5 hours and is then poured into 250 ml of distilled water and mixed with further separation of the organic layer.

(c) 200 ml of saturated solution of sodium bicarbonate is added to the resulting organic layer, and the mixture is left at room temperature, being intensely stirred, for 24 hours, in order to undergo hydrolysis resulting in a solution of 3'-N, 4',13-di-O-tri-trifluoroacetyldaunorubicinol.

(d) After completion of hydrolysis (controlled according to HPLC), the organic layer is separated and subjected to evaporation under reduced pressure conditions until fully dry.

(e) After evaporation, 5 grams of N-trifluoroacetyl-13-daunorubicinol is produced with a purity of about 90% (this is confirmed by HPLC).

(f) The N-trifluoroacetyl-13-daunorubicinol from step (e) of Example 1 is utilized in the next synthetic step in Example 2 without additional purification.

EXAMPLE 2

(a) 8 ml of DMSO is dissolved in 100 ml of DCM and chilled down to −60° C. while being stirred. After that, 2 ml of oxalylchloride in 5 ml of DCM is added to the solution, which is then incubated at −60° C. for 40 minutes to produce a reaction mixture.

(b) 5 grams of N-trifluoroacetyl-13-daunorubicinol is dissolved in 50 ml of DCM and is added to the reaction mixture over a 20-minute period, while maintaining the temperature in a −60±5° C. range. The reaction mixture is then incubated for 1 hour.

(c) 10 ml of triethylamine is added to the reaction mixture at a temperature ≤−60° C. The total time of contact between the reaction mixture and the triethylamine is 10 minutes.

(d) A solution of 5 ml of acetic acid in 10 ml of DCM is added to the reaction mixture and stirred for 2 minutes.

(e) The reaction mixture is then poured into 300 ml of distilled water. This is stirred and an organic layer is separated. This step is repeated 3 times.

(f) The organic layer is evaporated in a rotary evaporator under reduced pressure conditions.

(g) After evaporation, 4.7 gram of 4'keto-N-trifluoroacetyldaunorubicin is produced with a purity of about 85% (this is confirmed by HPLC).

(h) The 4'keto-N-trifluoroacetyldaunorubicin from step (g) of Example 2 is utilized in the next synthetic step in Example 3 without additional purification.

EXAMPLE 3

(a) 4.7 grams of 4'keto-N-trifluoroacetyldaunorubicin is dissolved in 180 ml of tetrahydrofuran and, while stirring, 2.1 grams of sodium triacetylborohydride is added over a 40-minute period. While being agitated, the reaction mixture is incubated for 1 hour at a temperature range of 20±2° C.

(b) The reaction mass is then transferred into a mixture of 150 ml of DCM+300 ml of distilled water+2 ml of 1M hydrochloric acid, and stirred. An organic layer is separated and then washed twice with 300 ml aliquots of distilled water.

(c) After evaporation, 4.6 g of 4'epi-N-trifluoroacetyldaunorubicin is produced with a purity of about 79% (this is confirmed by HPLC).

(d) The produced crude product then undergoes purification in a preparative chromatograph. After evaporation of the eluate, 3.0 grams of 4'epi-N-trifluoroacetyldaunorubicin is produced with a purity of about 95% (this is confirmed by HPLC).

EXAMPLE 4

3.0 grams of 4'epi-N-trifluoroacetyldaunorubicin is suspended in 200 ml of distilled water at a temperature 30° C., and 10 ml of 1.0N NaOH solution is then added. The mixture is incubated for 30 minutes, and then neutralized to pH 7 with a solution of hydrochloric acid and is then purified using preparative chromatography. After evaporation of eluate, 2.1 grams of 4'epi-daunorubicin hydrochloride is produced with a purity of about 96% (Confirmed by HPLC).

EXAMPLE 5

(a) 2.1 grams of 4'epi-daunorubicin hydrochloride is dissolved in 70 ml of dimethylformamide, and 2.8 grams of hydrogen dibromobromate bis (dimethylformamide) is added to the mixture. The mixture is then incubated at 40° C. for 2 hours.

(b) The reaction mixture is poured into 350 ml of acetonitrile. The precipitated sediment is filtered and washed with acetonitrile; and the solvent is removed.

(c) The solid sediment is dissolved in a mixture of 80 ml of acetone+80 ml of 0.25 M aqueous solution of hydrogen bromide+8 grams of sodium formate. The reaction mixture is incubated for 30 hours at 35° C.

(d) The reaction mixture undergoes preparative chromatography wherein epirubicin-containing fraction is separated.

(e) Eluate is evaporated, and the residue is crystallized by adding acetone.

(f) The yield of this process is 1.3 g of epirubicin hydrochloride of 99.8% purity (this is confirmed by HPLC).

We claim:

1. A method of preparing an anthracyclin having a formula represented by Formula (1)

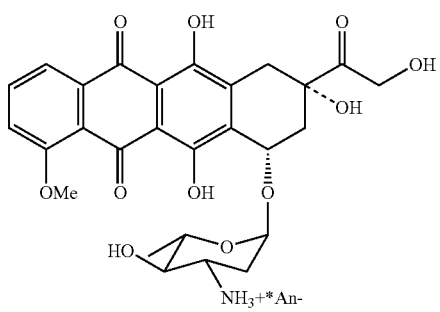

comprising:
(a) providing N-Trifluoroacetyl-13-daunorubicinol represented by Formula (4);

(b) reacting the N-Trifluoroacetyl-13-daunorubicinol with dimethylsulfoxide (DMSO) activated by an acylating agent, in an aprotic solvent, to produce an intermediate sulfoxy salt and treating the intermediate sulfoxy salt with a strong base to produce 4-'-keto-N-Trifluoroacetyldaunorubicin of Formula (5);

wherein the aprotic solvent is selected from the group consisting of DMSO, DMAA, HMPA, Acetonitrile, DCM, halogenalkanes, aromatic hydrocarbons, and mixtures thereof;
wherein the acylating agent is represented by AcX, wherein:
AcX=PySO$_3$, SOCl$_2$, PHal$_3$, POHal$_3$, wherein Hal=Cl, Br; or AcX is defined by the combination of Ac and X, wherein Ac=AlkCO, OC—(CH$_2$)—CO, n=0-4; AlkSO$_2$, ArCO, or ArSO$_2$; wherein Alk=alkyl of halogenalkyl radical; and Ar=phenyl or substituted phenyl radical; and X=Cl, Br, I, OAc;

wherein the strong base is a cyclic or polycyclic tertiary amine represented by NR$_7$R$_8$R$_9$, wherein R$_7$, R$_8$, and R$_9$=alkyl or cycloalkyl, and wherein, if R$_8$, R$_9$=cycloalkyl, then R$_8$ together with R$_9$ simultaneously=—(CH$_2$) where n=3-6;

(c) reacting the 4'-keto-N-Trifluoroacetyldaunorubicin with a borohydride of an alkaline metal to produce N-Trifluoroacetyl-4'-epi-daunorubicin represented by Formula (6);

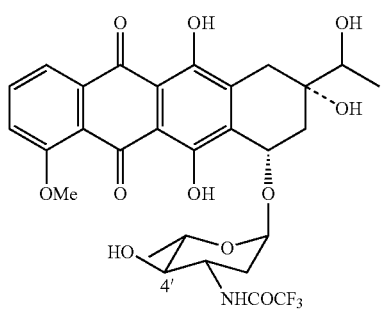

Formula 6

(d) hydrolyzing N-Trifluoroacetyl-4'-epi-daunorubicin in a basic solution to produce a compound represented by Formula (7); wherein An⁻ is an anion of a strong acid;

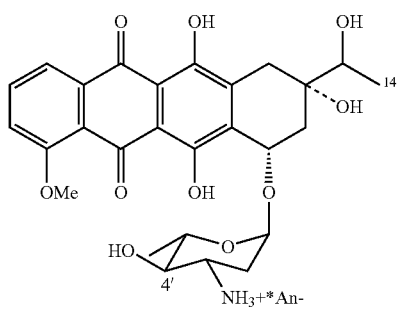

Formula 7

(e) reacting the compound represented by Formula (7) with a halogenizing agent represented by Formula (8),

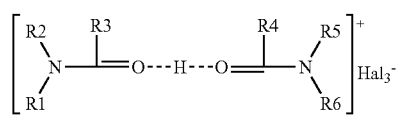

Formula 8 wherein R$_1$ through R$_6$ are defined as at least one of H or a hydrocarbon radical of 1 to 4 carbon chains (C$_1$-C$_4$) and Hal is Cl, Br, or I, to form a compound represented by Formula (9),

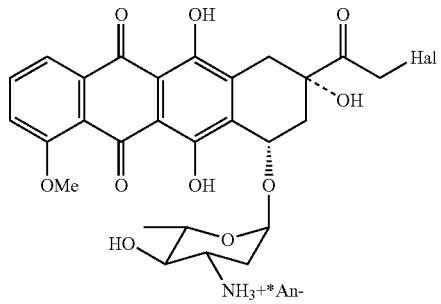

Formula 9 wherein Hal is Cl, Br, or I, and An– is an anion of strong acid; and (f) hydrolyzing the compound represented by Formula (9) in the presence of a formate of an alkaline metal to produce an anthracyclin having a formula represented by Formula (1),

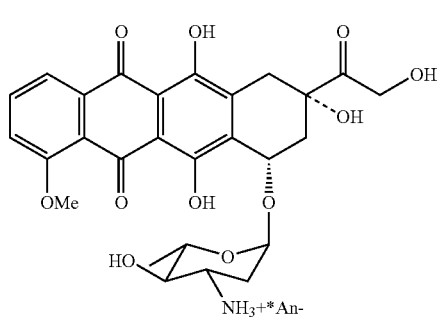

Formula 1

2. The method of claim 1, wherein the borohydride of an alkaline metal in step (c) is represented by MHBL$_3$, wherein M is one of Li, Na, or K, and L is one of AlkO, AlkCOO, ArCOO wherein Alk is one of Me, Et, n-Pr, All, —(CH$_2$)$_n$, n=0-4 and wherein Ar=Ph or substituted Ph=Ph-Alk.

3. The method of claim 1, wherein step (b) is carried out at a temperature within the range of about –80° C. to about 0° C.

4. The method of claim 1, wherein the reaction with the halogenizing agent is conducted at a temperature of about 20° C. to about 60° C. for between 2 to 20 hours.

5. The method of claim 1, where step (a) comprises:
providing 13-daunorubicinol represented by Formula (3)

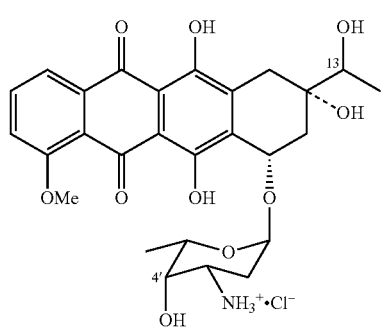

Formula 3 and
acylating by trifluoroacetic anhydride the 13-daunorubicinol in a solvent to produce the N-Trifluoroacetyl-13- daunorubicinol represented by Formula (4) provided in step (a).

6. The method of claim 5, wherein said solvent is dichloromethane.

7. The method of claim 5, wherein the borohydride of an alkaline metal in step (c) is represented by $MHBL_3$, wherein M is one of Li, Na, or K, and L is one of AlkO, AlkCOO, ArCOO wherein Alk is one of Me, Et, n-Pr, All, —$(CH_2)_n$, n=0-4 and wherein Ar=Ph or substituted Ph=Ph-Alk.

8. The method of claim 5, wherein step (b) is carried out at a temperature within the range of about —80° C. to about 0° C.

9. The method of claim 5, wherein the reaction with the halogenizing agent is conducted at a temperature of about 20° C. to about 60° C. for between 2 to 20 hours.

10. The method of claim 9, wherein said solvent is dichloromethane.

11. The method of claim 5, wherein:
step (b) is carried out at a temperature within the range of about --80° C. to about 0° C.;
the reaction with the halogenizing agent is conducted at a temperature of about 20° C. to about 60° C. for between 2 to 20 hours; and
said solvent used for acylating the 13-daunorubicinol to produce the N-Trifluoroacetyl-13-daunorubicinol represented by Formula (4) provided in step (a) is dichloromethane.

12. A method of preparing an anthracyclin having a formula represented by Formula (1)

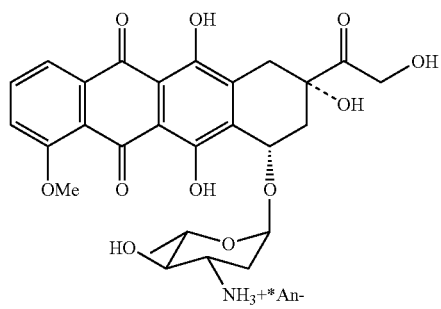

Formula 1 comprising:
(a) providing N-Trifluoroacetyl-13-daunorubicinol represented by Formula (4);

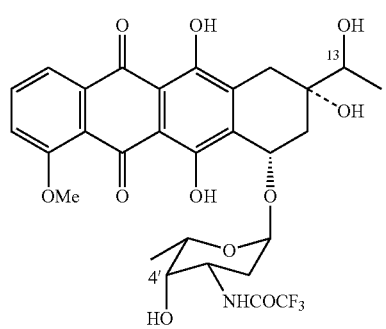

Formula 4

(b) reacting the N-Trifluoroacetyl-13-daunorubicinol with dimethylsulfoxide (DMSO) activated by an acylating agent, in an aprotic solvent, to produce an intermediate sulfoxy salt and treating the intermediate sulfoxy salt with a strong base to produce 4'-keto-N-Trifluoroacetyldaunorubicin of Formula (5);

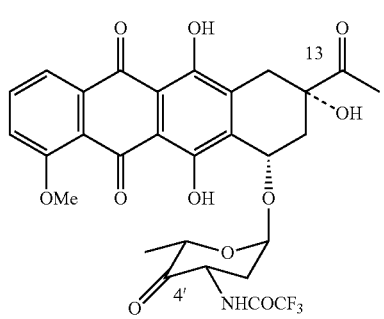

Formula 5 wherein the acylating agent is represented by AcX, wherein:
$AcX=PySO_3$, $SOCl_2$, $PHal_3$, $POHal_3$, wherein Hal=Cl, Br; or
AcX is defined by the combination of Ac and X, wherein Ac=AlkCO, OC—$(CH_2)_n$—CO, n=0-4; $AlkSO_2$, ArCO, or $ArSO_2$; wherein Alk=alkyl of halogenalkyl radical; and Ar=phenyl or substituted phenyl radical; and X=Cl, Br, I, OAc;
wherein the strong base is a cyclic or polycyclic tertiary amine represented by $NR_7R_8R_9$, wherein $R_7$, $R_8$, and $R_9$=alkyl or cycloalkyl, and wherein, if $R_8$, $R_9$=cycloalkyl, then $R_8$ together with $R_9$ simultaneously=—$(CH_2)_n$ where n=3-6;
(c) reacting the 4'-keto-N-Trifluoroacetyldaunorubicin with a borohydride of an alkaline metal to produce N-Trifluoroacetyl-4'-epi-daunorubicin represented by Formula (6);

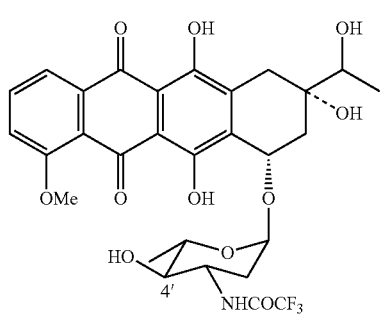

Formula 6

(d) hydrolyzing N-Trifluoroacetyl-4'-epi-daunorubicin in a basic solution to produce a compound represented by Formula (7); wherein An⁻ is an anion of a strong acid;

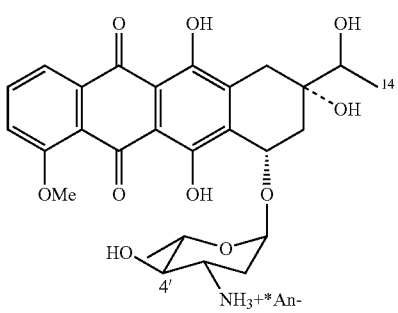

Formula 7

(e) reacting the compound represented by Formula (7) with a halogenizing agent represented by Formula (8),

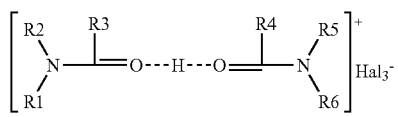

Formula 8 wherein $R_1$ through $R_6$ are defined as at least one of H or a hydrocarbon radical of 1 to 4 carbon chains ($C_1$-$C_4$) and Hal is Cl, Br, or I, to form a compound represented by Formula (9),

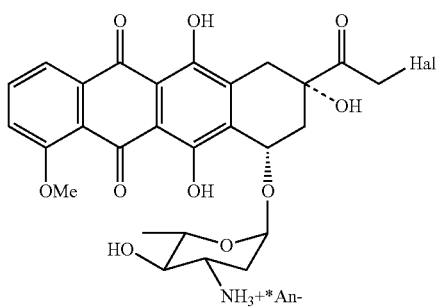

Formula 9 wherein Hal is Cl, Br, or I, and An⁻ is an anion of strong acid; and (f) hydrolyzing the compound represented by Formula (9) in the presence of a formate of an alkaline metal to produce an anthracyclin having a formula represented by Formula (1),

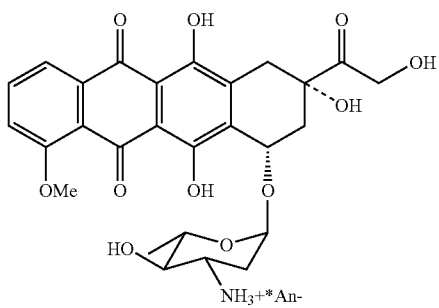

Formula 1

13. The method of claim 12, wherein step (b) is carried out at a temperature within the range of about −80° C to about 0° C.

14. The method of claim 12, wherein the reaction with the halogenizing agent is conducted at a temperature of about 20° C. to about 60° C. for between 2 to 20 hours.

15. The method of claim 12, wherein step (a) comprises:
providing 13-daunorubicinol represented by Formula (3)

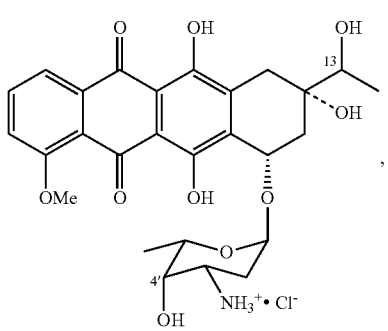

Formula 3 and
acylating by trifluoroacetic anhydride the 13-daunorubicinol in a solvent to produce the N-Trifluoroacetyl-13-daunorubicinol represented by Formula (4) provided in step (a).

16. The method of claim 15, wherein said solvent is dichloromethane.

17. The method of claim 1, wherein AcX=oxalylchloride.

18. The method of claim 17, wherein the strong base in step (b) comprises at least one of DBU, quinuclidine, or triethylamine.

19. The method of claim 17, wherein the strong base in step (b) is triethylamine.

20. The method of claim 1, wherein the strong base in step (b) comprises at least one of DBU, quinuclidine, or triethylamine.

21. The method of claim 1, wherein:
AcX=oxalylchloride;
the strong base in step (b) comprises at least one of DBU, quinuclidine, or triethylamine; and
the borohydride of an alkaline metal in step (c) is represented by $MHBL_3$, wherein M is one of Li, Na, or K, and L is one of AlkO, AlkCOO, ArCOO wherein Alk is one of Me, Et, n-Pr, or All (Allyl), and wherein Ar=Ph or substituted Ph=Ph-Alk.

22. The method of claim 17, wherein the borohydride of an alkaline metal in step (c) comprises sodium triacetyloxyborohydride.

23. The method of claim 18, wherein the basic solution in step (d) comprises sodium hydroxide.

24. The method of claim 19, wherein the halogenizing agent in step (e) comprises dimethylformamide and hydrogen dibromobromate bis.

25. The method of claim 24, wherein the formate of an alkaline metal in step (f) comprises sodium formate.

26. The method of claim 12, wherein AcX=oxalylchloride.

27. The method of claim 26, wherein the strong base in step (b) comprises at least one of DBU, quinuclidine, or triethylamine.

28. The method of claim 26, wherein the strong base in step (b) is triethylamine.

29. The method of claim 12, wherein the strong base in step (b) comprises at least one of DBU, quinuclidine, or triethylamine.

30. The method of claim 19, wherein:
AcX=oxalylchloride;
the strong base in step (b) comprises at least one of DBU, quinuclidine, or triethylamine; and
the borohydride of an alkaline metal in step (c) is represented by $MHBL_3$, wherein M is one of Li, Na, or K, and L is one of AlkO, AlkCOO, ArCOO wherein Alk is one of Me, Et, n-Pr, All, —($CH_2$), n=0-4 and wherein Ar=Ph or substituted Ph=Ph-Alk.

31. The method of claim 26, wherein the borohydride of an alkaline metal in step (c) comprises sodium triacetyloxyborohydride.

32. The method of claim 27, wherein the basic solution in step (d) comprises sodium hydroxide.

* * * * *